(12) United States Patent
Ciampini et al.

(10) Patent No.: US 11,357,540 B2
(45) Date of Patent: Jun. 14, 2022

(54) PORT FIXATION DEVICE

(71) Applicant: Covidien LP, Mansfield, MA (US)

(72) Inventors: Fabio Ciampini, Shelton, CT (US); Amanda Adinolfi, Wallingford, CT (US); Garrett Ebersole, Hamden, CT (US)

(73) Assignee: Covidien LP, Mansfield, MA (US)

( * ) Notice: Subject to any disclaimer, the term of this patent is extended or adjusted under 35 U.S.C. 154(b) by 391 days.

(21) Appl. No.: 16/265,223

(22) Filed: Feb. 1, 2019

(65) Prior Publication Data

US 2019/0254703 A1    Aug. 22, 2019

Related U.S. Application Data

(60) Provisional application No. 62/631,540, filed on Feb. 16, 2018.

(51) Int. Cl.
*A61B 17/34* (2006.01)
*A61B 17/00* (2006.01)
*A61M 25/02* (2006.01)

(52) U.S. Cl.
CPC ...... *A61B 17/3423* (2013.01); *A61B 17/3421* (2013.01); *A61B 2017/00862* (2013.01); *A61B 2017/3419* (2013.01); *A61B 2017/3492* (2013.01); *A61M 2025/024* (2013.01)

(58) Field of Classification Search
CPC .................. A61M 25/02; A61M 39/06; A61M 2025/0293; A61M 2039/0626; A61M 2025/024; A61M 2017/347; A61M 2039/062; A61B 17/3423; A61B 17/3421; A61B 2017/00862; A61B 2017/3419; A61B 2017/348; A61B 2017/3492; A61B 17/34; A61B 17/3419
See application file for complete search history.

(56) References Cited

U.S. PATENT DOCUMENTS 3,253,594 A    5/1966   Matthews et al.
4,699,616 A   10/1987   Nowak et al.
5,226,890 A    7/1993   Ianniruberto et al.
(Continued)

OTHER PUBLICATIONS

Extended European Search Report dated May 6, 2019 issued in corresponding EP Appln. No. 19157517.4-1113.

*Primary Examiner* — Bhisma Mehta
*Assistant Examiner* — Hong-Van N Trinh
(74) *Attorney, Agent, or Firm* — Carter, DeLuca & Farrell LLP

(57) ABSTRACT

A port fixation device is disclosed and includes a body portion and a plug. The body portion includes a circular portion, a first tab, and a second tab. The circular portion defines an aperture which is configured to allow a surgical access port to extend therethrough. The first tab and the second tab are disposed in mechanical cooperation with the circular portion. Movement of the first tab with respect to the second tab from a first position to a second position causes a diameter of the aperture to change from a first size to a second size. The first size is smaller than the second size, and the first position of the first tab is its rest position. The plug is disposed in mechanical engagement with the body portion, and has sufficient elasticity to remain engaged with the body portion when the first tab is in the first position and in the second position.

9 Claims, 6 Drawing Sheets

(56) References Cited

U.S. PATENT DOCUMENTS

| | | |
|---|---|---|
| 5,263,939 A | 11/1993 | Wortrich |
| 5,269,754 A | 12/1993 | Rydell |
| 5,312,351 A | 5/1994 | Gerrone |
| 5,358,488 A | 10/1994 | Suriyapa |
| 5,407,427 A | 4/1995 | Zhu et al. |
| 5,445,615 A | 8/1995 | Yoon |
| 5,484,420 A | 1/1996 | Russo |
| 5,713,869 A | 2/1998 | Morejon |
| 5,792,112 A | 8/1998 | Hart et al. |
| 5,836,913 A | 11/1998 | Orth et al. |
| 7,300,448 B2 | 11/2007 | Criscuolo et al. |
| 7,691,089 B2 | 4/2010 | Gresham |
| 7,824,419 B2 | 11/2010 | Boraiah |
| 8,109,943 B2 | 2/2012 | Boraiah et al. |
| 8,137,322 B2 | 3/2012 | Soltz et al. |
| 8,147,453 B2 | 4/2012 | Albrecht et al. |
| 8,287,503 B2 | 10/2012 | Albrecht et al. |
| 10,022,149 B2 | 7/2018 | Holsten et al. |
| 2002/0016556 A1 | 2/2002 | Williams |
| 2003/0153926 A1* | 8/2003 | Schmieding ....... A61B 1/00154 606/108 |
| 2003/0158572 A1 | 8/2003 | McFarlane |
| 2003/0187424 A1 | 10/2003 | Chu et al. |
| 2004/0138702 A1 | 7/2004 | Peartree et al. |
| 2006/0079918 A1 | 4/2006 | Creston |
| 2009/0030443 A1 | 1/2009 | Buser et al. |
| 2010/0057010 A1* | 3/2010 | Goransson ......... A61B 17/3417 604/164.04 |
| 2010/0094393 A1 | 4/2010 | Cordeiro et al. |
| 2014/0257356 A1 | 9/2014 | Pacak et al. |
| 2018/0085145 A1 | 3/2018 | Okoniewski et al. |
| 2018/0206883 A1* | 7/2018 | McIntyre ........... A61B 17/3421 |

\* cited by examiner

PORT FIXATION DEVICE

CROSS-REFERENCE TO RELATED APPLICATIONS

This application claims the benefit of and priority to U.S. Provisional Patent Application No. 62/631,540 filed Feb. 16, 2018, the entire disclosure of which is incorporated by reference herein.

BACKGROUND

Technical Field

The present disclosure relates to a surgical apparatus. More particularly, the present disclosure relates to a port fixation device for maintaining a surgical access port in a fixed position during a surgical procedure.

Background of Related Art

In minimally invasive surgical procedures, including endoscopic and laparoscopic surgeries, a surgical access port permits the introduction of a variety of surgical instruments into a body cavity or opening. A surgical access port (e.g., a cannula) is introduced through an opening in tissue (i.e. a naturally occurring orifice or an incision) to provide access to an underlying surgical site in the body. The incision is typically made using an obturator having a blunt or sharp tip that has been inserted within the passageway of the surgical access port. For example, a cannula has a tube of rigid material with a thin wall construction, through which an obturator may be passed. The obturator is utilized to penetrate a body wall, such as an abdominal wall, or to introduce the surgical access port through the body wall, and is then removed to permit introduction of surgical instrumentation through the surgical access port to perform the surgical procedure.

These procedures may present issues with respect to maintaining the position of the surgical access port with respect to the body wall, particularly, when exposed to a pressurized environment.

SUMMARY

The present disclosure relates to a port fixation device including a body portion and a plug. The body portion includes a circular portion, a first tab, and a second tab. The circular portion defines an aperture which is configured to allow a surgical access port to extend therethrough. The first tab is disposed in mechanical cooperation with the circular portion. The second tab is disposed in mechanical cooperation with the circular portion. Movement of the first tab with respect to the second tab from a first position to a second position causes a diameter of the aperture to change from a first size to a second size. The first size is smaller than the second size, and the first position of the first tab is its rest position. The plug is disposed in mechanical engagement with the body portion, and has sufficient elasticity to remain engaged with the body portion when the first tab is in the first position and in the second position.

In disclosed embodiments, the port fixation device may include a biasing element disposed in mechanical cooperation with the body portion. The biasing element may be configured to urge the first tab toward the first position. It is further disclosed that the biasing element may be in contact with the first tab and with the second tab. It is also disclosed that the biasing element may be disposed between the first tab and the second tab, and may be in contact with the first tab and the second tab. In embodiments, the biasing element may be a metal spring. Other biasing elements can be used such as elastomeric or polymeric components.

It is further disclosed that the circular portion may include a notch therein configured to facilitate the diameter of the aperture changing from the first size to the second size.

In embodiments, the first tab may be pivotable with respect to the second tab.

It is also disclosed that the port fixation device may include a first leg extending from the circular portion and a second leg extending from the circular portion. In embodiments, the first tab may include a finger extending therefrom, and the finger is in contact with the first leg and the second leg. It is further disclosed that the finger or cam member may be configured to move along the first leg and along the second leg as the first tab moves with respect to the second tab.

In disclosed embodiments, the plug may be made from an elastomeric material. It can be molded from a polymeric material, and can also be a foam. It is further disclosed that at least a portion of the plug may be frusto-conically shaped.

BRIEF DESCRIPTION OF THE DRAWINGS

Various embodiments of the present disclosure are illustrated herein with reference to the accompanying drawings, wherein.

DETAILED DESCRIPTION OF THE EMBODIMENTS

Figure 1A:
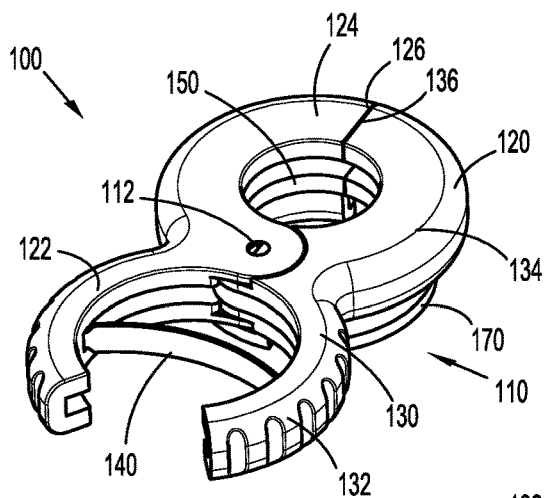
FIGS. 1a, 1b, and 1c are perspective views of a port fixation device of the present disclosure.

Embodiments of the presently disclosed port fixation device are described in detail with reference to the drawings, wherein like reference numerals designate corresponding elements in each of the several views.

Various embodiments of a port fixation device are described herein. Generally, a port fixation device engages a surgical access port (e.g., a cannula) to help maintain the position of the surgical access port with respect to the patient, e.g., when exposed to a pressurized environment and improve manipulability. Generally, the various port fixation devices described herein are configured to accommodate a surgical access port having an outside diameter that is greater than a minimum size of the diameter of the aperture defined by the body, thereby allowing a pressure-tight seal therebetween.

Referring to FIGS. 1a, 1b, 1c, and 2, a first embodiment of a port fixation device is shown and indicated by reference character 100. Port fixation device 100 includes a body 110, a biasing element 140, and a plug 180. Body 110 includes a first portion 120 and a second portion 130. First portion 120 of body 110 includes a first tab 122 and a first end 124. Second portion 130 of body 110 includes a second tab 132 and a second end 134. Body 110 defines an aperture 150 adjacent and between first end 124 and second end 134 that is configured to allow a surgical access port to pass through.

First portion 120 of body 110 and second portion 130 of body 110 are movable (e.g., pivotable) with respect to each other (e.g., about a common pivot 112) between a first configuration where respective edges 126, 136 of first portion 120 and second portion 130 are closest to each other (i.e., minimum spacing), and a second configuration where edges 126, 136 are farthest from each other (i.e., maximum spacing).

First tab 122 is disposed on the opposite side of pivot 112 from first end 124, and second tab 132 is disposed on the opposite side of pivot 112 from second end 134. Biasing element 140 (e.g., a metal spring) is positioned between first tab 122 and second tab 132 and generally urges or biases first tab 122 away from second tab 132, thereby urging or biasing edge 126 of first portion 120 of body 110 and edge 136 of second portion 120 of body toward each other in the general direction of arrows "A" about pivot 112. Thus, biasing element 140 helps maintain body 110 in the first configuration where a diameter of aperture 150 is smallest. When body 110 is in the first, biased or rest configuration, first end 124 and second end 134 are clamped onto an appropriately sized surgical access port inserted through aperture 150. In this configuration, body 110 frictionally engages an outer wall of the surgical access port and provides a pressure-tight seal. This can also tamponade bleeding from the incision.

To move body 110 of port fixation device 100 from its first configuration to its second configuration, a user moves first tab 122 toward second tab 132 (or vice versa) in the general direction of arrows "B" against the bias of biasing element 140. This approximation of first tab 122 and second tab 132 causes edge 126 of first portion 120 and edge 136 of second portion 120 to move or pivot away from each other about pivot 112 in the general direction of double-headed arrow "C," thereby increasing the diameter of aperture 150. When body 110 is in the second, unbiased configuration, the larger diameter of aperture 150 allows the surgical access port to be inserted through and removed from aperture 150.

Figure 1B:
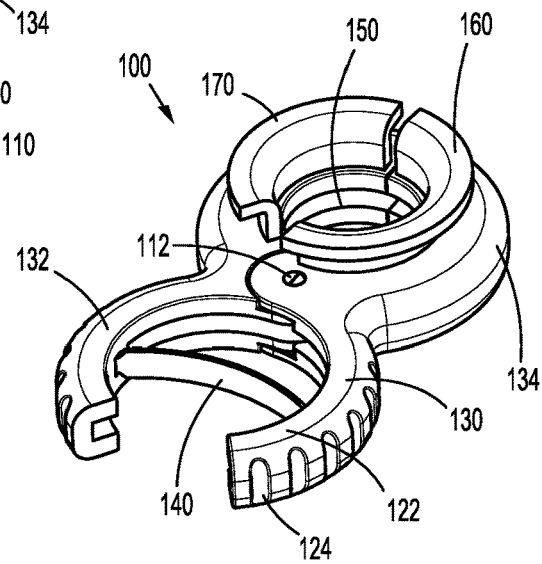
Figure 1C:
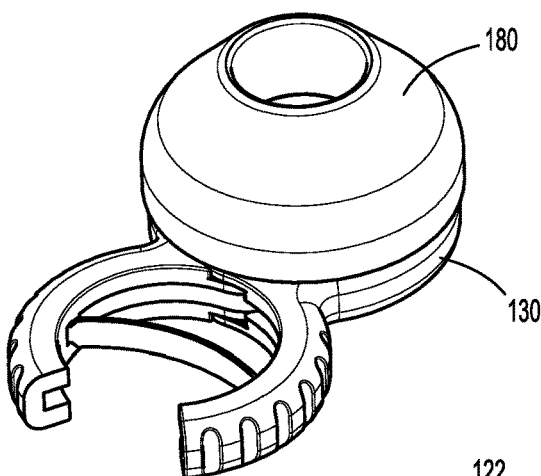
Figure 2:
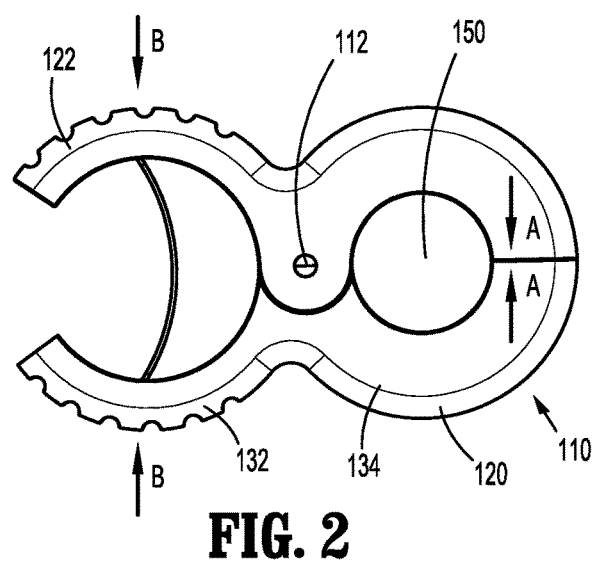
FIG. 2 is a top plan view of the port fixation device of FIGS. 1a, 1b and 1c.

With particular reference to FIGS. 1b and 1c, port fixation device 100 also includes a first wing 160 depending downwardly from first end 124 of first portion 120, and a second wing 170 depending downwardly from second end 134 of second portion 130. First wing 160 and second wing 170 are configured to allow plug 180 to be coupled thereto. Plug 180 includes a conical or frusto-conical shape and may be made from an elastomeric material or foam, for example. Plug 180 is configured to be at least partially inserted into the patient's incision to seal the incision from loss of pressure from a pressurized environment, for example, and to help maintain engagement between port fixation device 100 and the patient. Due to the elasticity of plug 180, plug 180 is able to maintain its engagement with first wing 160 and second wing 170 both when body 110 is in its first configuration and its second configuration.

In any of the embodiments disclosed herein, it is contemplated that the device includes suture tie structures. The suture tie structures will protrude from the body of the port fixation device and allow the device to be tethered down to the patient's skin with a loop of suture.

Referring to FIGS. 3a, 3b, 3c, and 4, a second embodiment of a port fixation device is shown and indicated by reference character 200. Port fixation device 200 includes a body 210 and a plug 280. Body 210 includes a first tab 220, a second tab 230, and a circular portion 240 interconnecting the first tab 220 and the second tab 230. Circular portion 240 includes a lip 244 extending downwardly and outwardly therefrom. Circular portion 240 and lip 244 define an aperture 250 which allows a surgical access port to pass through.

A notch 242 is defined in circular portion 240, and a slot 246 is defined in lip 244. Both notch 242 and slot 246 are disposed opposite circular portion 240 from a common pivot 212 where the first tab 220 contacts (or nearly contacts) the second tab 230.

First tab 220 of body 210 and second tab 230 of body 210 are movable with respect to each other about pivot 212 between a first position where notch 242 is narrowest and where slot 246 is narrowest, and a second position where notch 242 is widest and where slot 246 is widest. In the first position of first tab 220 and second tab 230, aperture 250 is smallest, and in the second position of first tab 220 and second tab 230, aperture 250 is largest.

First tab 220 and second tab 230 are naturally biased or at rest in the first position where a diameter of aperture 250 is smallest. In this position (i.e., the first configuration of body 210), circular portion 240 and lip 244 are clamped onto an appropriately sized surgical access port inserted through aperture 250 thereby forming a pressure-tight seal with an outer surface of the surgical access port.

To move body 210 of port fixation device 200 from its first configuration to its second configuration, a user moves first tab 220 toward second tab 230 (or vice versa) in the general direction of arrows "D" against the natural bias of first tab 220 and second tab 230. This approximation of first tab 220 and second tab 230 causes a first edge 242a of notch 242 and a second edge 242b of notch 242 to move away from each other, and causes a first edge 246a of slot 246 and a second edge 246b of slot 246 to move away from each other in the general direction of double-headed arrow "E" thereby increasing the diameter of aperture 250.

When body 210 is in the second, unbiased configuration, the larger diameter of aperture 250 allows the surgical access port to be inserted through and removed from aperture 250.

Figure 3A:
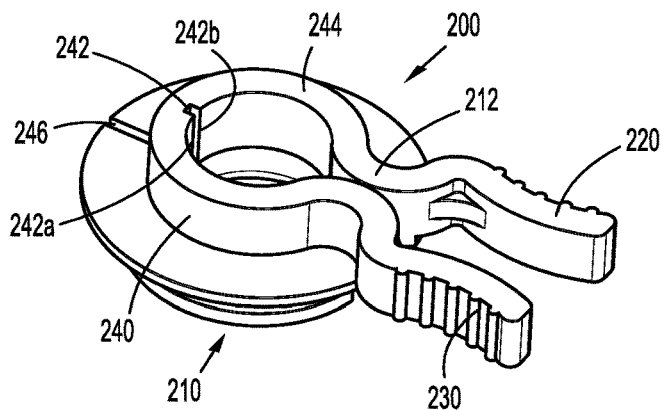
FIGS. 3a, 3b, and 3c are perspective views of a port fixation device in accordance with another embodiment of the present disclosure.
Figure 3B:
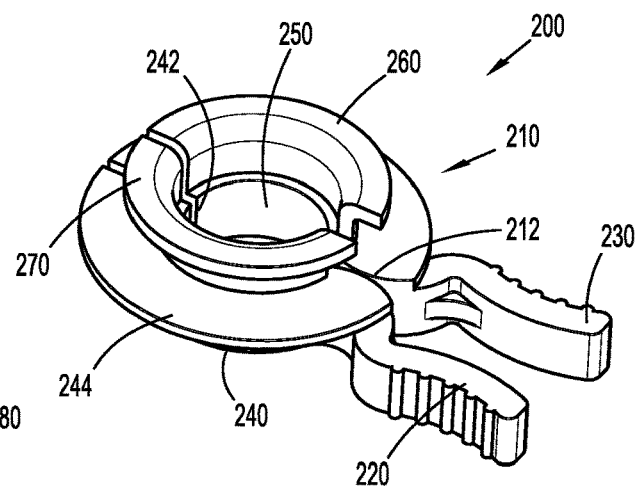
Figure 3C:
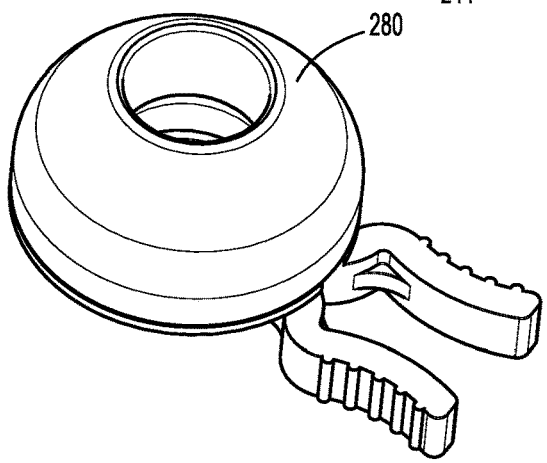
Figure 4:
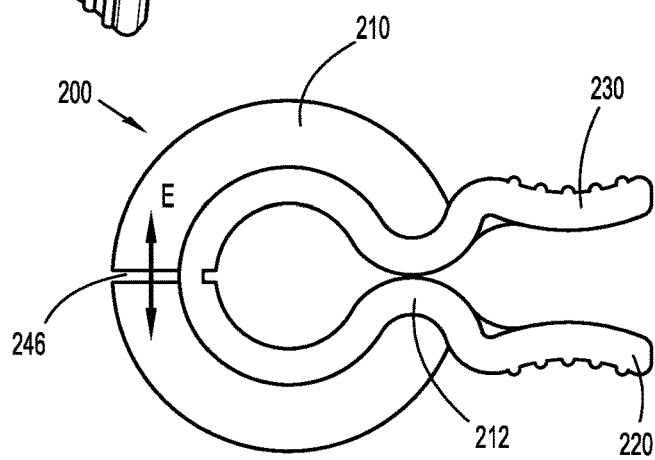
FIG. 4 is a top plan view of the port fixation device of FIGS. 3a, 3b and 3c.

With particular reference to FIGS. 3b and 3c, port fixation device 200 also includes a first wing 260 depending downwardly from one side of circular portion 240 and a second wing 270 depending downwardly from another side of circular portion 240. First wing 260 and second wing 270 are configured to allow plug 280 to be coupled thereto. Alternatively, the plug can be overmolded onto the body. Plug 280 includes a conical or frusto-conical shape and may be made from an elastomeric material or foam, for example.

Plug 280 is configured to be at least partially inserted into the patient's incision to seal the incision from loss of pressure from a pressurized environment, for example, and to help maintain engagement between port fixation device 200 and the patient. Due to the elasticity of plug 280, plug 280 is able to maintain its engagement with first wing 260 and second wing 270 both when body 210 is in its first configuration and its second configuration.

Referring to FIGS. 5a, 5b, 5c, and 6, a third embodiment of a port fixation device is shown and indicated by reference character 300. Port fixation device 300 includes a body 310 and a plug 380. Body 310 includes a first tab 320, a second tab 330, and a circular portion 340 interconnecting the first tab 320 and the second tab 330. Circular portion 340 includes a lip 344 extending downwardly and outwardly therefrom. Circular portion 340 and lip 344 define an aperture 350 which allows a surgical access port to pass through. Circular portion 340 includes a pair of legs 342a, 342b extending at an angle therefrom, which define a gap 345 therebetween. First tab 320 includes a finger or cam member 322 extending therefrom. Finger 322 is positioned at least partially within gap 345 and in contact with both legs 342a, 342b. Further options include having a retaining feature on legs 342a and 342b to lock the position of the finger/ball 322 when tab 320 is pressed. Another option includes the finger/ball 322 with ratchet teeth on either side to ratchet into ridges on the surface of legs 342a and 342b. Other structures are contemplated to allow fixation of the device in an open position. For example, the finger or ball 322 can have tatchet teeth on one or both sides to engage ridges on the surface of one or both legs 342a, 342b.

A notch 343 is defined in circular portion 340, and a slot 346 is defined in lip 344. Both notch 343 and slot 346 are configured to allow circular portion 340 and lip 344 to expand, contract and/or flex.

First tab 320 of body 310 is movable toward second tab 330 of body 310 from a first configuration where aperture 350 is smallest, to a second configuration where aperture 350 is largest.

First tab 320 is naturally biased or at rest in the first configuration where a diameter of aperture 350 is smallest. In this configuration (i.e., the first configuration of body 310), circular portion 340 and lip 344 are clamped onto an appropriately sized surgical access port inserted through aperture 350.

To transition body 310 of port fixation device 300 from its first configuration to its second configuration, a user moves first tab 320 toward second tab 330 in the general direction of arrow "F" (while exerting pressure on second tab 330 toward first tab 320). This approximation of first tab 320 toward second tab 330 causes finger 322 of first tab 320 to move along legs 342a, 342b of circular portion 340 toward a center of aperture 350, thereby causing legs 342a, 342b to move away from each other and resulting in increasing the diameter of aperture 350.

When body 310 is in the second, unbiased configuration, the larger diameter of aperture 350 allows the surgical access port to be inserted through and removed from aperture 350.

Figure 5A:
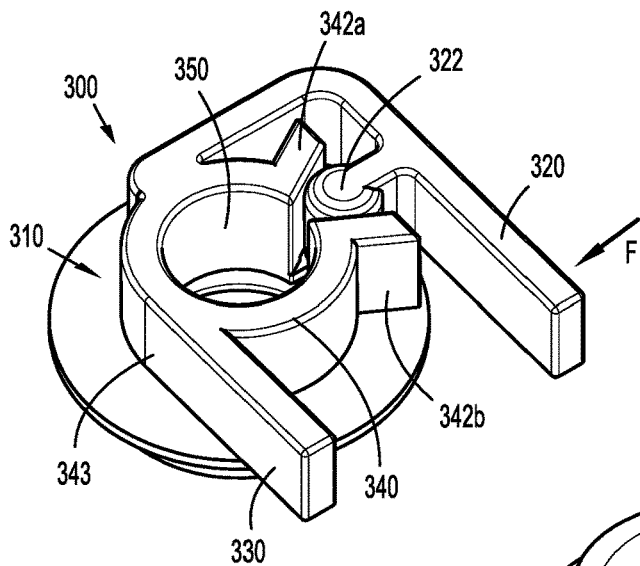
FIGS. 5a, 5b, and 5c are a perspective views of a port fixation device in accordance with another embodiment of the present disclosure.
Figure 5B:
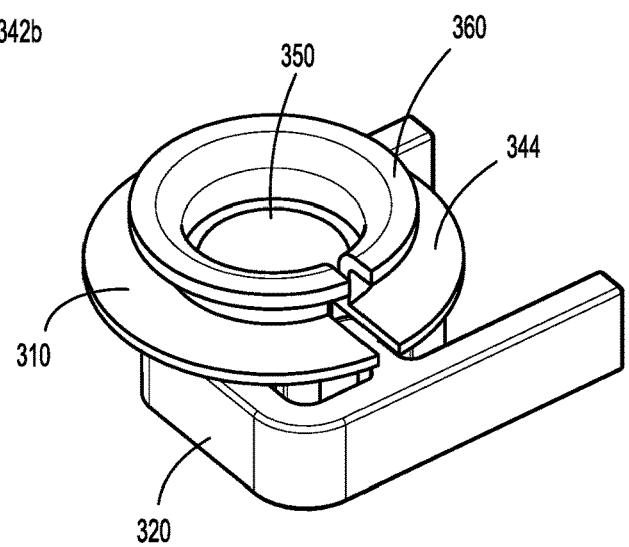
Figure 5C:
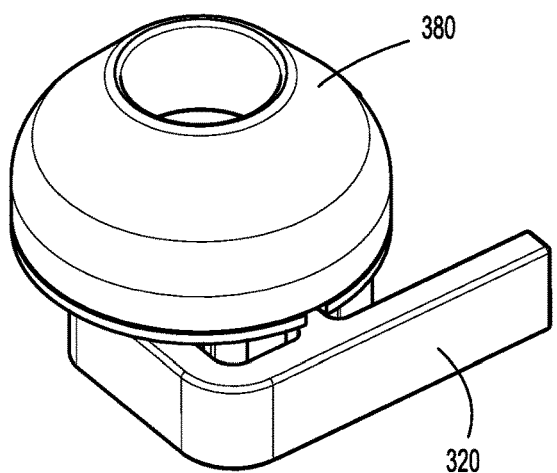
Figure 6:
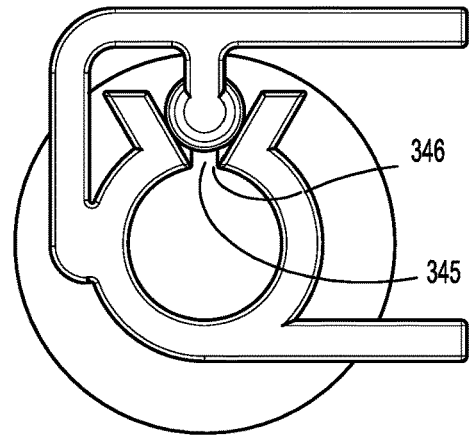
FIG. 6 is a top plan view of the port fixation device of FIGS. 5a, 5b, and 5c.

With particular reference to FIGS. 5b and 5c, port fixation device 300 also includes a wing 360 depending downwardly from circular portion 340. Wing 360 is configured to allow plug 380 to be coupled thereto. Plug 380 includes a conical or frusto-conical shape and may be made from an elastomeric material or foam, for example. Plug 380 is configured to be at least partially inserted into the patient's incision to seal the incision from loss of pressure from a pressurized environment, for example, and to help maintain engagement between port fixation device 300 and the patient. Due to the elasticity of plug 380, plug 380 is able to maintain its engagement with wing 360 both when body 310 is in its first configuration and its second configuration.

Figure 7:
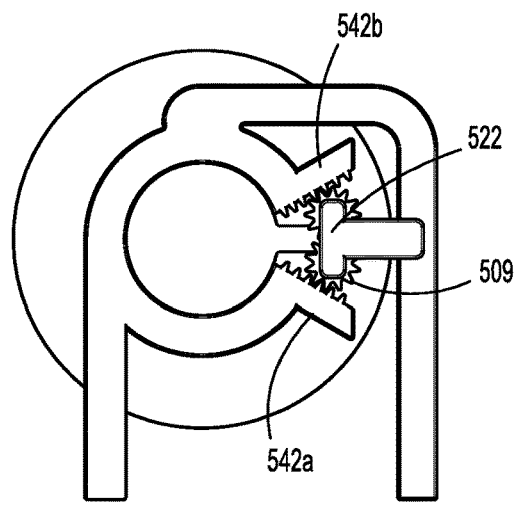
FIG. 7 is a plan view of another port fixation device.
Figure 8:
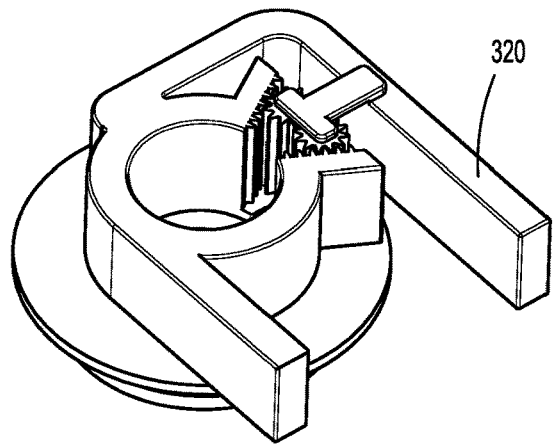
FIG. 8 is a perspective view of the port fixation device of FIG. 7.

In further embodiments, the port fixation device according to any of the embodiments described herein can include a locking feature which allows the device to remain in the open, non-engaging configuration, allowing the user to more easily slide the device onto a surgical access device or port. FIGS. 7 and 8 show a further embodiment of a port fixation device that has gear-like teeth on the surfaces of the legs 542a, 542b and the finger 522. The teeth are inter-engaging surfaces and can have other shapes. The teeth 509 releasably lock the position of the device so that it remains open. Overcoming the friction of the teeth 509 allows the user to change the device to the initial configuration in which the device clamps onto an appropriately sized surgical access device or port.

Figure 9:
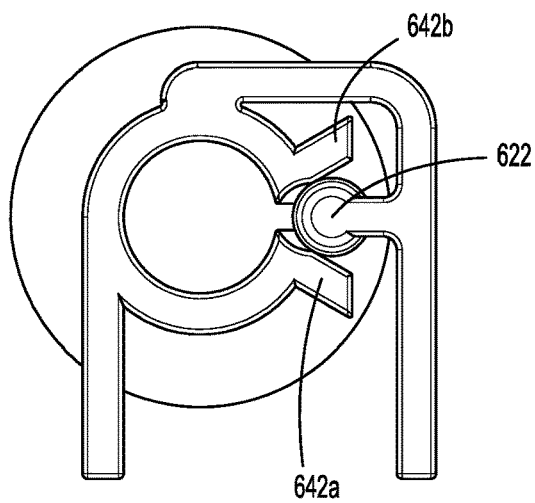
FIG. 9 is a plan view of another port fixation device.
Figure 10:
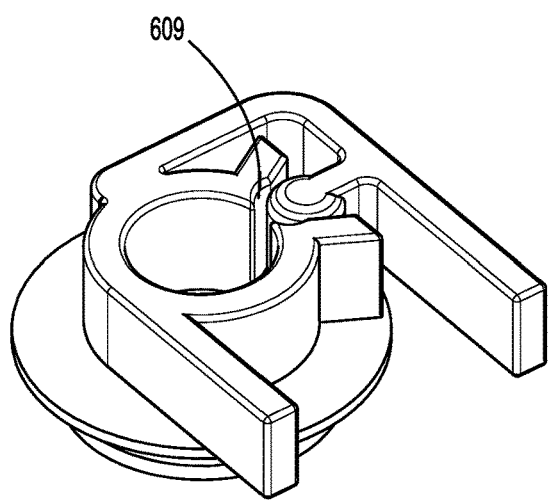
FIG. 10 is a perspective view of the port fixation device of FIG. 9.

FIGS. 9 and 10 show a further embodiment of a port fixation device that has shaped recesses on the surfaces of the legs 642a, 642b and the finger 622. The recesses 609 releasably lock the position of the device so that it remains open, acting like a detent. Overcoming the friction of the recesses 609 allows the user to change the device to the initial configuration in which the device clamps onto an appropriately sized surgical access device or port.

Referring to FIGS. 11a, 11b, 11c, and 12, a fourth embodiment of a port fixation device is shown and indicated by reference character 400. Port fixation device 400 includes a body 410 and a plug 480. Body 410 includes a tab 420, an engagement portion 430 or second tab, and a circular portion 440. Engagement portion 430 forms part of circular portion 440. Circular portion 440 includes a lip 444 extending downwardly and outwardly therefrom. Circular portion 440 and lip 444 define an aperture 450 which allows a surgical access port to pass through.

Circular portion 440 includes a pair of legs 442a, 442b extending at an angle therefrom, which define a gap 445 therebetween. Tab 420 extends from leg 442a and includes a finger 422 extending therefrom. Finger 422 is positioned at least partially within gap 445 and in contact with both legs 442a, 442b.

A pair of notches 443 is defined in circular portion 440, and a slot 446 is defined in lip 444. Both notches 443 and slot 446 are configured to allow circular portion 440 and lip 444 to expand, contract and/or flex.

Tab 420 of body 410 is movable toward engagement portion 430 of body 410 from a first configuration where aperture 450 is smallest, to a second configuration where aperture 450 is largest.

Tab 420 is naturally biased or at rest in the first position where a diameter of aperture 450 is smallest. In this position (i.e., the first configuration of body 410), circular portion 440 and lip 444 are clamped onto an appropriately sized surgical access port inserted through aperture 450.

To transition body 410 of port fixation device 400 from its first configuration to its second configuration, a user moves tab 420 toward engagement portion 430 in the general direction of arrow "G" (while exerting pressure on engagement portion 430 toward tab 420). This movement of tab 420 toward engagement portion 430 causes finger 422 of tab 420 to move along legs 442a, 442b of circular portion 440 toward a center of aperture 450, thereby causing legs 442a, 442b to move away from each other and resulting in increasing the diameter of aperture 450.

When body 410 is in the second, unbiased configuration, the larger diameter of aperture 450 allows the surgical access port to be inserted through and removed from aperture 450.

Figure 11A:
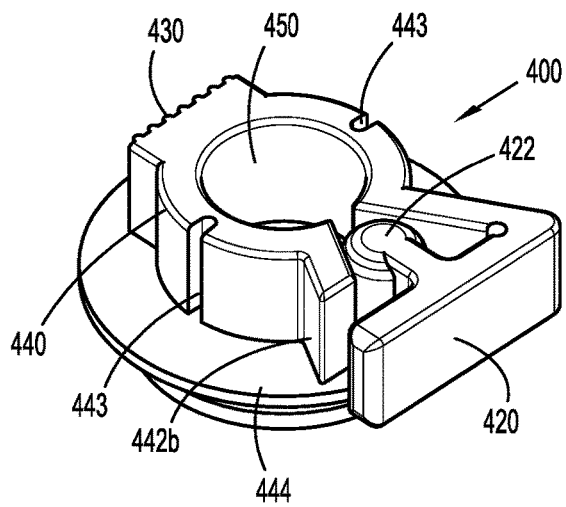
FIGS. 11a, 11b, and 11c are perspective view a of a port fixation device including a plug in accordance with another embodiment of the present disclosure.
Figure 11B:
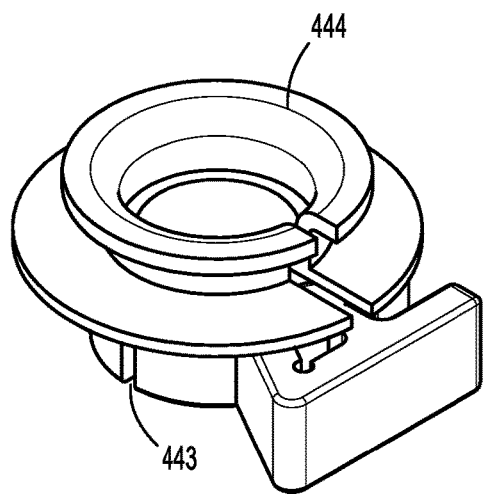
Figure 11C:
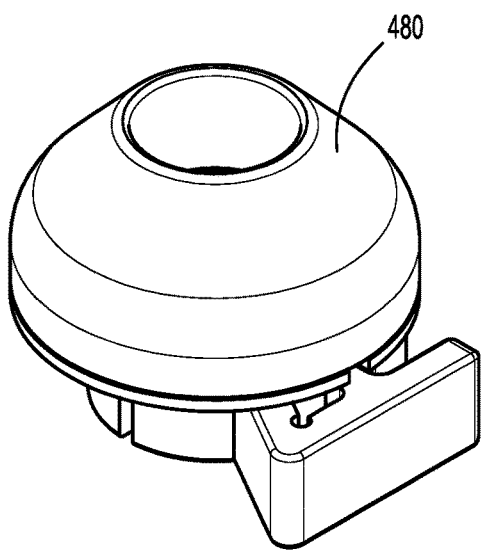
Figure 12:
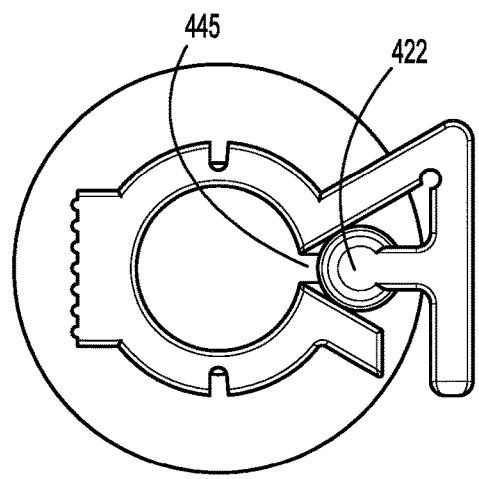
FIG. 12 is a top plan view of the port fixation device of FIGS. 11a, 11b, and 11c.

As shown in FIG. 11b, port fixation device 400 also includes a wing 460 depending downwardly from circular portion 440. Wing 460 is configured to allow plug 480 (FIG. 11c) to be coupled thereto. Plug 480 includes a conical or frusto-conical shape and may be made from an elastomeric material or foam, for example. Plug 480 is configured to be at least partially inserted into the patient's incision to seal the incision from loss of pressure from a pressurized environment, for example, and to help maintain engagement between port fixation device 400 and the patient. Due to the flexibility of plug 480, plug 480 is able to maintain its engagement with wing 460 both when body 410 is in its first configuration and its second configuration.

Figure 13:
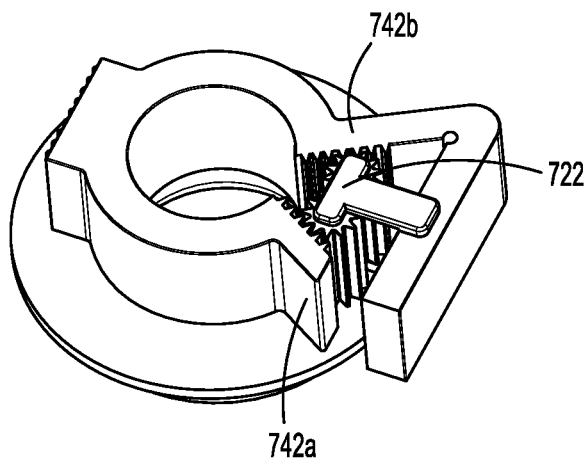
FIG. 13 is a perspective view of another port fixation device.
Figure 14:
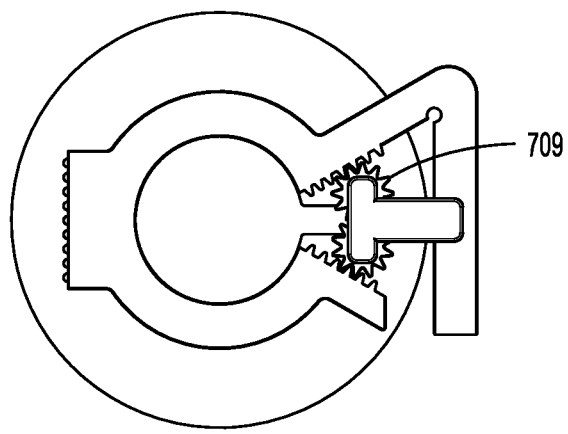
FIG. 14 is a plan view of the port fixation device of FIG. 14.

FIGS. 13 and 14 show a further embodiment of a port fixation device that has gear-like teeth on the surfaces of the legs 742a, 742b and the finger 722. The teeth are inter-engaging surfaces and can have other shapes. The teeth 709 releasably lock the position of the device so that it remains open. Overcoming the friction of the teeth 709 allows the user to change the device to the initial configuration in which the device clamps onto an appropriately sized surgical access device or port.

Figure 15:
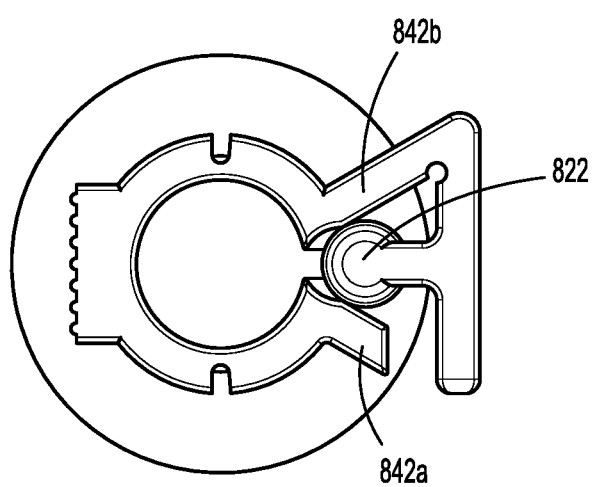
FIG. 15 is a perspective view of another port fixation device.
Figure 16:
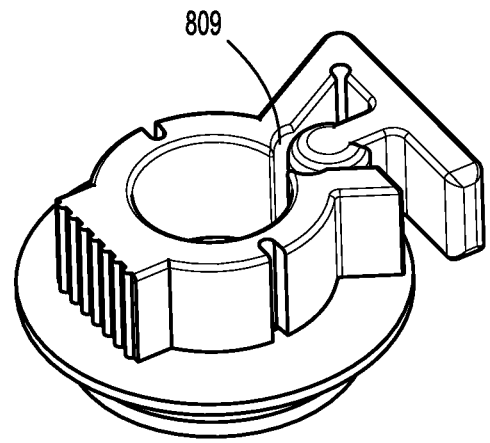
FIG. 16 is a plan view of the port fixation device of FIG. 15.

FIGS. 15 and 16 show a further embodiment of a port fixation device that has shaped recesses on the surfaces of the legs 842a, 842b and the finger 822. The recesses 809 releasably lock the position of the device so that it remains open, acting like a detent. Overcoming the friction of the recesses 609 allows the user to change the device to the initial configuration in which the device clamps onto an appropriately sized surgical access device or port.

In any of the embodiments disclosed herein, the device can have a body with a recess or opening allowing for resilient movement to a relative open position, or can include a metal spring or other biasing member, or both. In this way, a surgical access port or cannula assembly can be conveniently engaged and disengaged by the fixation device.

While the above description contains many specifics, these specifics should not be construed as limitations on the scope of the present disclosure, but merely as illustrations of various embodiments thereof. Therefore, the above description should not be construed as limiting, but merely as exemplifications of various embodiments. Those skilled in the art will envision other modifications within the scope and spirit of the claims appended hereto

The invention claimed is:

1. A port fixation device, comprising:
a body portion including:
    a circular portion defining an aperture, the aperture is configured to allow a surgical access port to extend therethrough;
    a first tab disposed in mechanical cooperation with the circular portion; and
    a second tab disposed in mechanical cooperation with the circular portion, wherein movement of the first tab with respect to the second tab from a first position to a second position causes a diameter of the aperture to change from a first size to a second size, wherein the first size is smaller than the second size, and wherein the first position of the first tab is its rest position; and
a plug disposed in mechanical engagement with the body portion, the plug having sufficient elasticity to remain engaged with the body portion when the first tab is in the first position and in the second position, wherein the plug forms a continuous ring when the first tab is in the second position, and a frusto-conical portion of the plug is made from an elastomeric material.

2. The port fixation device according to claim 1, further comprising a biasing element disposed in mechanical cooperation with the body portion, the biasing element configured to urge the first tab toward the first position.

3. The port fixation device according to claim 2, wherein the biasing element is in contact with the first tab.

4. The port fixation device according to claim 3, wherein the biasing element is in contact with the second tab.

5. The port fixation device according to claim 2, wherein the biasing element is disposed between the first tab and the second tab, and is in contact with the first tab and the second tab.

6. The port fixation device according to claim 2, wherein the biasing element is a metal spring.

7. The port fixation device according to claim 1, wherein the first tab is pivotable with respect to the second tab.

8. The port fixation device according to claim 1, wherein the plug forms the continuous ring when the first tab is in the first position.

9. The port fixation device according to claim 1, wherein the plug forms a closed aperture when the first tab is in the first position and when the first tab is in the second position.

* * * * *